United States Patent
Karamanoglu et al.

(10) Patent No.: US 8,805,511 B2
(45) Date of Patent: Aug. 12, 2014

(54) METHOD AND APPARATUS TO DETECT SUBCEREBRAL ISCHEMIA

(75) Inventors: Mustafa Karamanoglu, Fridley, MN (US); Vincent E. Splett, Apple Valley, MN (US); Nancy J. Rakow, Oak Grove, MN (US); Linnea R. Lentz, Stacy, MN (US)

(73) Assignee: Medtronic, Inc., Minneapolis, MN (US)

( * ) Notice: Subject to any disclaimer, the term of this patent is extended or adjusted under 35 U.S.C. 154(b) by 113 days.

(21) Appl. No.: 13/192,029

(22) Filed: Jul. 27, 2011

(65) Prior Publication Data
US 2013/0030495 A1    Jan. 31, 2013

(51) Int. Cl.
*A61N 1/08* (2006.01)

(52) U.S. Cl.
USPC ............................................. 607/42; 607/20

(58) Field of Classification Search
USPC ...................................... 607/20, 42
See application file for complete search history.

(56) References Cited

U.S. PATENT DOCUMENTS

| | | | |
|---|---|---|---|
| 4,694,834 A | 9/1987 | Meyerhoff | |
| 5,047,208 A | 9/1991 | Schweitzer | |
| 5,231,986 A | 8/1993 | Bennett | |
| 5,824,029 A | 10/1998 | Weijand | |
| 6,006,134 A * | 12/1999 | Hill et al. | 607/9 |
| 6,076,015 A | 6/2000 | Hartley et al. | |
| 7,471,970 B2 | 12/2008 | Zhang | |
| 8,011,367 B2 | 9/2011 | Lurie et al. | |
| 2002/0188332 A1 | 12/2002 | Lurie et al. | |
| 2004/0209307 A1 | 10/2004 | Valkirs | |
| 2008/0161878 A1 | 7/2008 | Tehrani | |
| 2010/0185253 A1 | 7/2010 | Dimarco et al. | |

FOREIGN PATENT DOCUMENTS

WO    2010/083059 A2    7/2010

* cited by examiner

*Primary Examiner* — Joseph Dietrich
(74) *Attorney, Agent, or Firm* — Carol F. Barry (57) ABSTRACT

A medical device and associated method detect ischemia using stimulation delivered to induce respiration. A spontaneous breathing response to the stimulation-induced respiration is determined. Ischemia is detected in response to the spontaneous breathing response. The spontaneous breathing response is measured as a response to adjusting a parameter controlling the stimulation.

15 Claims, 10 Drawing Sheets

METHOD AND APPARATUS TO DETECT SUBCEREBRAL ISCHEMIA

TECHNICAL FIELD

The disclosure relates generally to a method and apparatus for detecting ischemia and, more particularly, to a method and apparatus for detecting subcerebral ischemia.

BACKGROUND

Subcerebral ischemia may occur as a result of thrombus, heart failure associated with low cardiac output, cardiac arrhythmias, low blood pressure or other cardiovascular events. Subcerebral ischemia may manifest as a stroke or transient ischemic episode. Methods for detecting subcerebral ischemia may include Magnetic Resonance Imaging (MRI), Positron Emission Technology (PET), or biological marker measurements taken from the patient's blood. These methods can be time-consuming, costly, or not readily available. Even with sophisticated imaging technology, the detection of subcerebral ischemia can be challenging. A need remains for an apparatus and method for detecting subcerebral ischemia.

DETAILED DESCRIPTION

In the following description, references are made to illustrative embodiments. It is understood that other embodiments may be utilized without departing from the scope of the disclosure. The term "subcerebral" as used herein includes any central nervous system (CNS) structures involved in respiratory function.

Methods described herein deliver stimulation to cause activation of the diaphragm to induce respiration. A spontaneous breathing response to the induced respiration is measured and used in detecting ischemia. The ischemia may be a systemic ischemic condition or a more localized ischemic condition. The detected ischemia involves at least a portion of the CNS, in particular the ischemic condition affects the subcerebral structures involved in controlling respiration. During reduced cerebral blood flow, such as during subcerebral ischemia, the sensitivity to changes in blood oxygen saturation, carbon dioxide saturation, and blood pH may increase. Induced respiration by stimulating the phrenic nerve(s) or diaphragm modulates the oxygen and carbon dioxide levels in the blood. The spontaneous breathing response to induced respiration may therefore provide indications of increased sensitivity of CNS chemoreceptors, thus indicating subcerebral ischemia.

Figure 1:
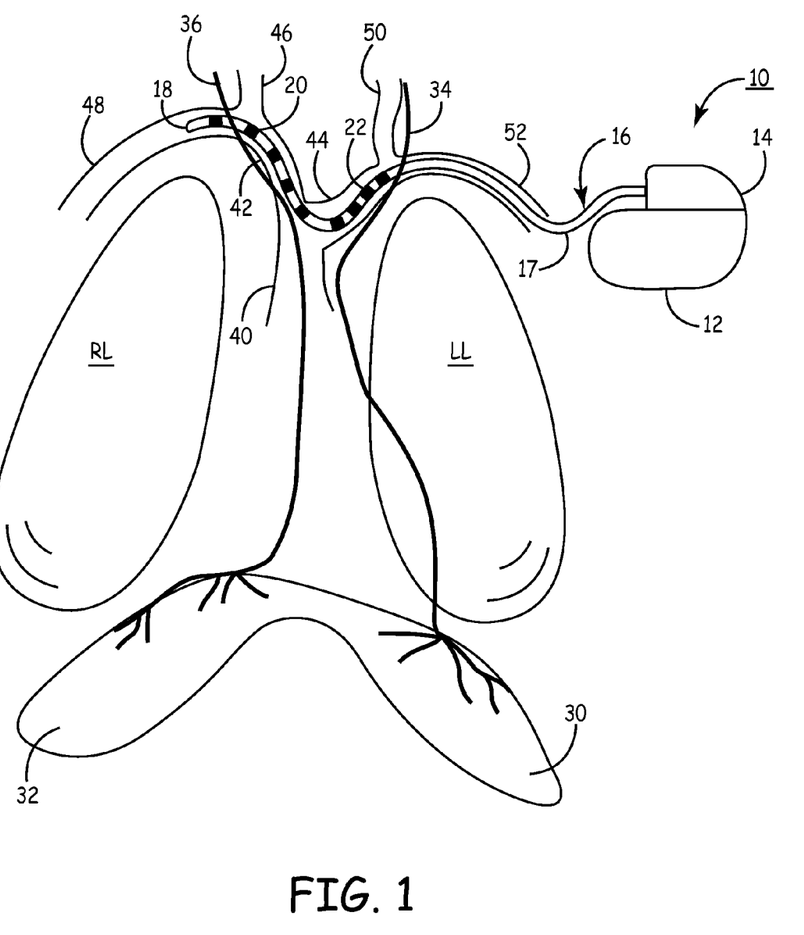
FIG. 1 is a schematic view of an implantable medical device (IMD) system for delivering phrenic nerve stimulation for activating the diaphragm to induce respiration.

FIG. 1 is a schematic view of an implantable medical device (IMD) system for delivering phrenic nerve stimulation (PNS) for activating the diaphragm to induce respiration. IMD 10 includes a housing 12 enclosing electronic circuitry (not shown) included in IMD 10 and a connector block 14 having at least one connector bore for receiving at least one medical electrical lead 16. Connector bores included in block 14 provide electrical connection between electrodes carried by lead 16 and IMD internal electronic circuitry.

In FIG. 1, the left phrenic nerve 34 and the right phrenic nerve 36 are shown innervating the respective left diaphragm 30 and right diaphragm 32. The anatomical locations of the left phrenic nerve 34, the right phrenic nerve 36 and other anatomical structures shown schematically in the drawings presented herein are intended to be illustrative of the approximate and relative locations of such structures. These structures are not necessarily shown in exact anatomical scale or location. The left phrenic nerve 34 is shown schematically to extend in close proximity to the left internal jugular vein (LJV) 50, the left subclavian vein (LSV) 52, and the left innominate vein (LIV) 44, also referred to as the left brachiocephalic vein.

The anatomical location of the right phrenic nerve 36 is shown schematically to extend in close proximity to the right internal jugular vein (RJV) 46, the right subclavian vein (RSV) 48, the right innominate vein (RIV) 42 (also referred to as the right brachiocephalic vein), and the superior vena cava (SVC) 40.

Lead 16 is a multipolar lead carrying proximal electrodes 22 and distal electrodes 20 at or near the distal end 18 of lead 16. In one embodiment, at least one proximal bipolar pair of electrodes is provided for stimulating the left phrenic nerve 34 and at least one distal bipolar pair of electrodes is provide for stimulating the right phrenic nerve 36. In various embodiments, two or more electrodes may be positioned along spaced apart locations adjacent the distal tip of lead 16 from which at least one pair of electrodes is selected for delivering stimulation to the right phrenic nerve 36. Additionally, two or more electrodes may be positioned along spaced apart locations proximally from the distal electrodes 20 from which at least one pair of electrodes is selected for delivering stimulation to the left phrenic nerve 34.

Lead 16 includes an elongated lead body 17, which may have a diameter in the range of approximately 2 French to 8 French, and typically approximately 4 French to approximately 6 French. The lead body 17 carries the electrodes 20 and 22 which are electrically coupled to electrically insulated conductors extending from individual respective electrodes 20 and 22 to a proximal connector assembly adapted for connection to IMD connector block 14. Lead 16 may be provided with a fixation element for fixing the position of the lead once a desired implant location is identified. Exemplary leads that can be useful for the present disclosure include U.S. Pat. No. 5,922,014, U.S. Pat. No. 5,628,778, U.S. Pat. Nos. 4,497,326, 5,443,492, or U.S. Pat. No. 7,860,580 such that electrodes are added and/or spaced apart in a manner similar to that disclosed in the figures of the present application, all of which are incorporated by reference in their entirety. Additional lead and electrode configurations that may be adapted for use with the present disclosure by adjusting lead shape, length, electrode number and/or electrode to effectively provide phrenic nerve stimulation as described herein are generally disclosed in U.S. Pat. No. 7,031,777, U.S. Pat. No. 6,968,237, and US Publication No. 2009/0270729, all of which are incorporated herein by reference in their entirety.

In one embodiment, distal tip 18 of lead 16 is advanced to a location along the RIV 42 and further along the RSV 48 or the RJV 46 to position distal electrodes 20 in operative relation to right phrenic nerve 36 for delivering stimulation pulses to nerve 36 to activate the right diaphragm 32. The proximal electrodes 22 may be appropriately spaced from distal electrodes 20 such that proximal electrodes 22 are positioned along the LIV 44 and/or along the junction of the LSV 52 and LJV 50 for delivering stimulation pulses to the left phrenic nerve 34 to activate the left diaphragm 30.

In various embodiments, lead 16 may carry four or more electrodes spaced at selected distances to provide at least one pair near a distal lead tip 18 for right phrenic nerve stimulation and at least one pair more proximally for left phrenic nerve stimulation. In other embodiments, lead 16 may carry multiple electrodes spaced equally along a portion of the body of lead 16 such that any pair may be selected for right phrenic nerve stimulation and any pair may be selected for left phrenic nerve stimulation based on the relative locations of the electrodes from the nerves.

Figure 2:
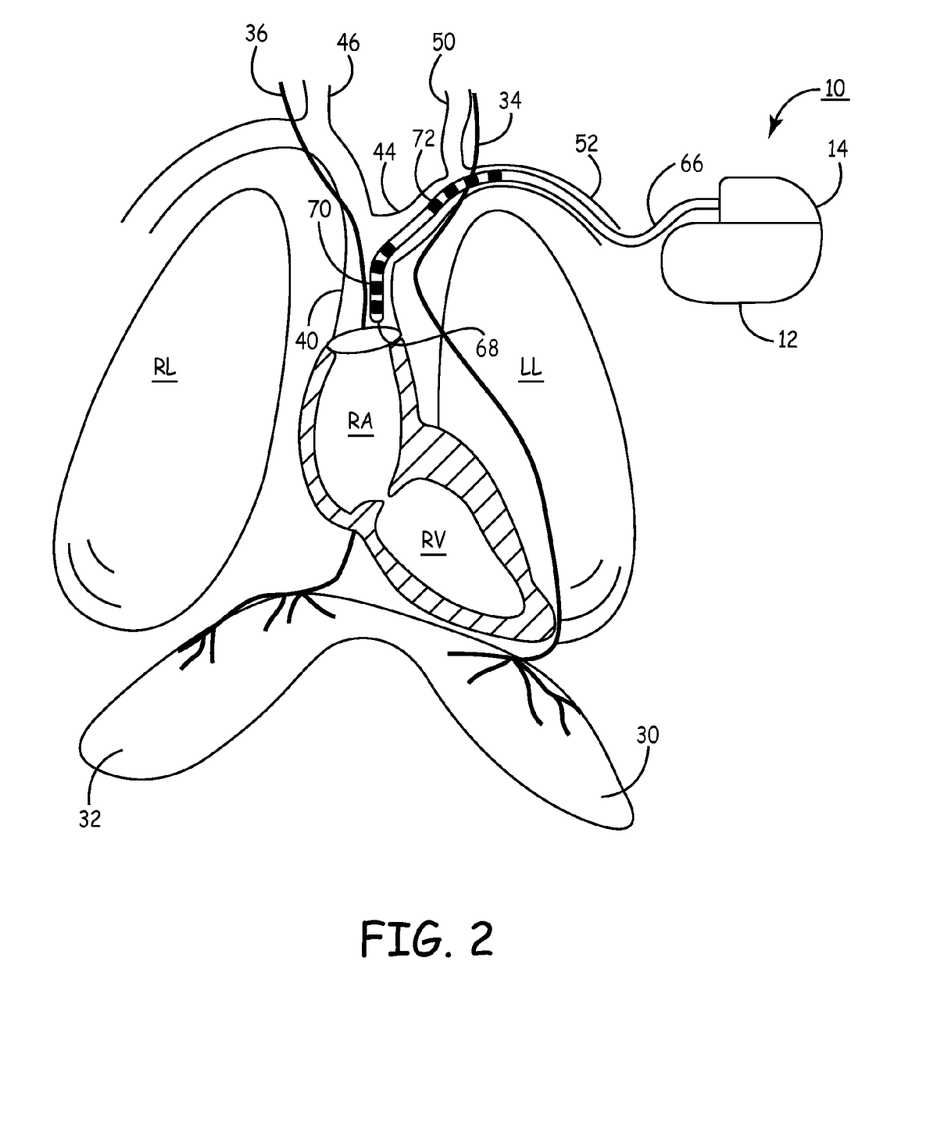
FIG. 2 is a schematic view of an IMD system for delivering phrenic nerve stimulation according to an alternative embodiment.

FIG. 2 is a schematic view of an IMD system for delivering PNS according to an alternative embodiment. In FIG. 2, the right atrium (RA) and the right ventricle (RV) are shown schematically in a partially cut-away view. The right phrenic nerve 36 extends posteriorly along the SVC 40, the RA and the inferior vena cava (IVC) (not shown in FIG. 2). The left phrenic nerve 34 normally extends along a left lateral wall of the left ventricle (not shown). The SVC 40 enters the RA. A lead 66 is coupled to IMD 10 via connector block 14. Lead 66 carries multiple electrodes that may be spaced apart into a plurality of distal electrodes 70 located near distal lead tip 68 and a plurality of proximal electrodes 72. The distal tip 68 of lead 66 is advanced into SVC 40 to position distal electrodes 70 in the SVC for stimulating the right phrenic nerve 36, which extends posteriorly to SVC 40 and the RA. The proximal electrodes 72 are used to stimulate the left phrenic nerve 34, e.g. along the LIV 44 or junction of the LJV 50 and LSV 52.

Figure 3:
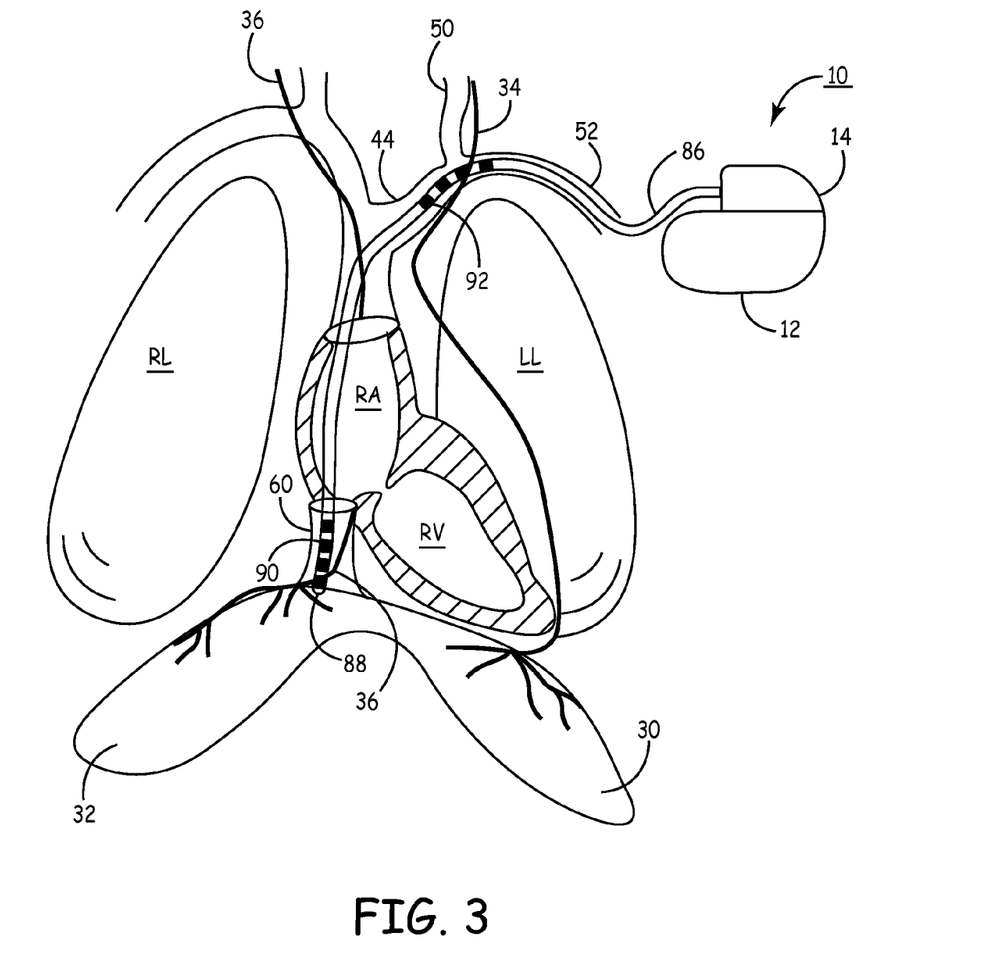
FIG. 3 is a schematic view of an IMD system for delivering phrenic nerve stimulation according to another alternative embodiment.

FIG. 3 is a schematic view of an IMD system for delivering PNS according to another alternative embodiment. In FIG. 3, the inferior vena cava (IVC) 60, which empties into the RA, is shown schematically. In this embodiment, lead 86 extends from IMD connector block 14 to the IVC 60 to position electrodes 90 adjacent distal lead tip 88 in the IVC 60 adjacent the right phrenic nerve 36 near the level of the diaphragm, e.g. approximately at the height of the eighth thoracic vertebra (T8) (not shown). Proximal electrodes 92 are positioned proximally along lead 86 for positioning along the LIV 44 or the junction of the LJV 50 and LSV 52 for providing stimulation to the left phrenic nerve 34.

Electrodes used for stimulating the right phrenic nerve and electrodes used for stimulating the left phrenic nerve are shown configured along a common lead in FIGS. 1 through 3. In alternative embodiments it is contemplated that two leads, one for stimulating the left and one for stimulating the right phrenic nerve, may be provided separately.

The housing 12 of IMD 10 may be provided as an indifferent electrode for use in combination with any of the lead-based electrodes shown in FIGS. 1 through 3 for some monitoring purposes. The electrodes included in an IMD system for delivering stimulation to induce respiration may additionally be used for sensing impedance signals. In some embodiments, the housing 12 may provide an indifferent electrode for delivering a drive current during thoracic impedance measurements or used in a measurement pair for monitoring thoracic impedance. Thoracic impedance measurements may be used to measure a respiratory response to stimulation, for example for estimating tidal volume or minute ventilation.

It is further recognized that additional leads and electrodes may be included in an IMD system capable of delivering PNS or more generally diaphragm stimulation. For example, IMD 10 may be coupled to cardiac leads, which may be subcutaneous leads, transvenous leads positioned in or along a heart chamber, or epicardial leads. IMD 10 may incorporate sensing electrodes along housing 12. IMD 10 may be provided specifically for delivering PNS (with associated monitoring of sensed signals for detecting ischemia) or may include other therapy delivery capabilities such as cardiac pacing (e.g. for bradycardia pacing, cardiac resynchronization in therapy, or anti-tachycardia pacing) cardioversion/defibrillation shocks, drug delivery or the like. As such, the IMD system may include other leads, electrodes and/or catheters not shown in FIGS. 1-3 related to other IMD functions.

In some embodiments, electrodes used for delivering PNS could be carried by leads that additionally carry cardiac pacing, sensing and/or defibrillation electrodes. In other embodiments, sensing electrodes carried by cardiac leads may be used for sensing EGM signals to control the timing of PNS.

In FIGS. 1 through 3, IMD 10 is shown in a left pectoral position such that it is the distal electrodes, e.g. electrodes 20, 70 or 90, that are positioned in operative relation to the right phrenic nerve 36 and the proximal electrodes, e.g. electrodes 22, 72 or 92, that are positioned in operative relation to the left phrenic nerve 34. Depending on the implanted configuration, lead 16 may be positioned entering a vein from a right venous approach such that it is the distal electrodes that are positioned for left phrenic nerve stimulation and the proximal electrodes that are positioned for right phrenic nerve stimulation. For example, IMD 10 may be implanted in a pocket along a right pectoral position, along a right or left abdominal position, centrally, or other implant location. The IMD implant location may determine whether it is the proximal electrodes or the distal electrodes that are positioned for stimulating the right or the left phrenic nerves, when the electrodes are all carried by a single phrenic nerve stimulation lead.

For example, a right-sided implantation of IMD 10 could include distal electrodes positioned along the LIV 44 for left phrenic nerve stimulation and proximal electrodes positioned for right phrenic nerve stimulation along the RIV 42 or junction of the RSV 48 and RJV 46.

Illustrative IMD systems and associated methods described herein for inducing respiration and monitoring a spontaneous breathing response for detecting ischemia include systems that deliver transvenous phrenic nerve stimulation. It is recognized that stimulation of the phrenic nerves directly, e.g., using a nerve cuff electrode, or stimulation of the diaphragm directly could be performed to induce respiration causing modulation of blood oxygen and carbon dioxide levels, which in turn will cause an associated spontaneous breathing response which may be evalutated for detecting ischemia. As such, systems in which the ischemia detection methods described herein may be implemented are not limited to fully implantable systems or systems that rely only on transvenous PNS. Systems that use external or temporarily implanted leads and electrodes for direct or indirect stimulation of the phrenic nerves and/or diaphragm may be used to induce respiration. Methods for controlling the stimulation of the phrenic nerves and/or diaphragm, sensing the spontaneous breathing response, and analyzing the spontaneous breathing response for detecting ischemia may be implemented in a fully implantable device, in an external device receiving signals from sensors implanted in or on the patient's body, or a combination of implantable and external system components.

Furthermore, while methods in the illustrative embodiments described herein rely on electrical stimulation for activating the diaphragm to induce respiration, it is recognized that alternative methods for activating the diaphragm can involve mechanical or chemical methods for causing depolarization of the phrenic nerve and diaphragm muscle.

Figure 4:
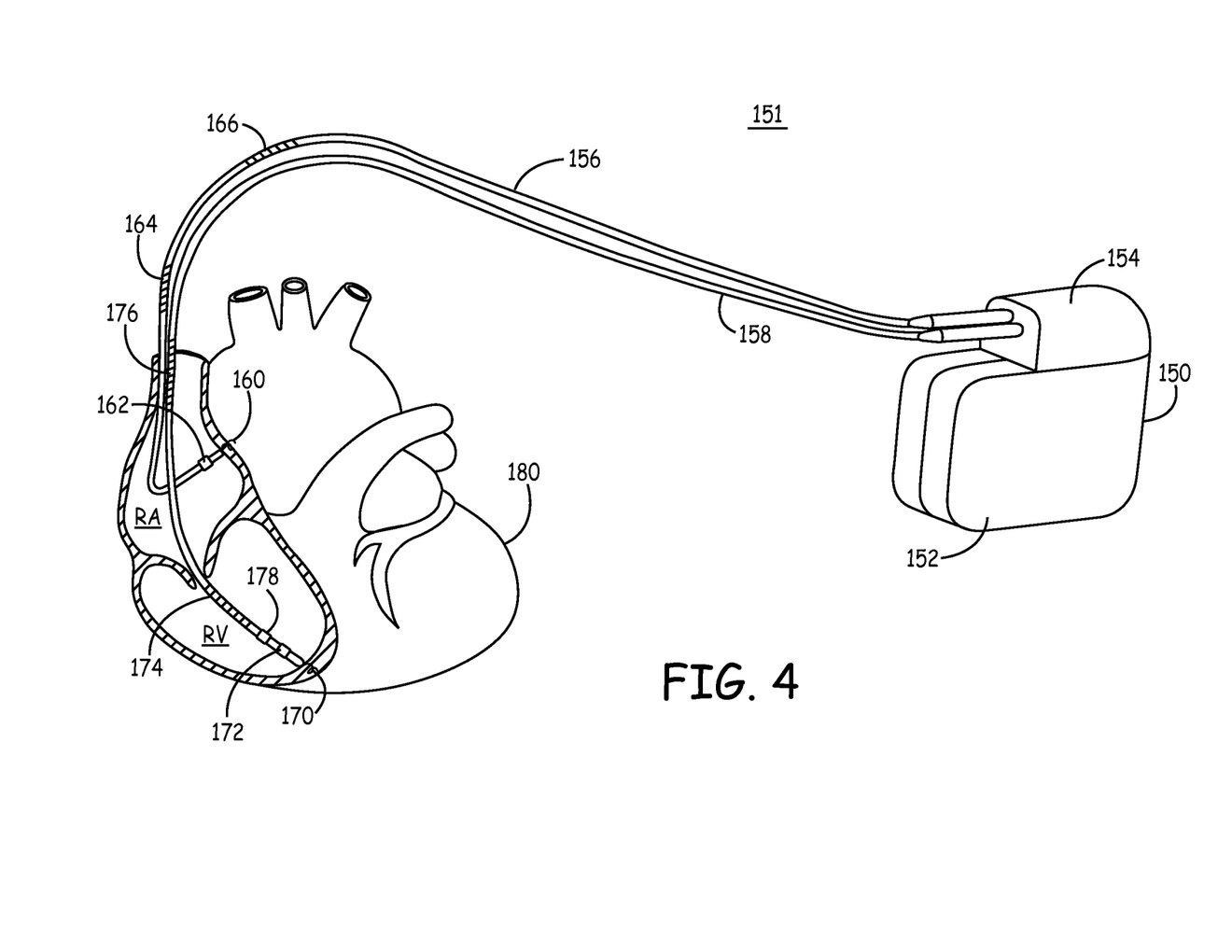
FIG. 4 is a schematic diagram of an IMD system that includes phrenic nerve stimulation capabilities for ischemia detection and cardiac therapy delivery capabilities.

FIG. 4 is a schematic diagram of an IMD system 151 that includes phrenic nerve stimulation capabilities for ischemia detection and cardiac therapy delivery capabilities. IMD 150 is shown embodied as an implantable cardiovertor defibrillator (ICD) capable of delivering both cardiac pacing and cardioversion/defibrillation shocks. IMD 150 may alternatively be embodied as a pacemaker, drug delivery pump, or may provide autonomic nerve stimulation for treating a cardiac condition.

IMD 150 is coupled to a patient's heart 180 by a right atrial lead 156 and a right ventricular lead 158. IMD 150 senses intrinsic heart activity, detects cardiac arrhythmias, and delivers cardiac stimulation pulses, as appropriate, to one or more heart chambers in response to detecting an arrhythmia. IMD 150 is further configured to detect ischemia using PNS and may provide a cardiac therapy in response to detecting ischemia.

The heart is shown in a partially cut-away view illustrating an upper heart chamber, the right atrium (RA), and a lower heart chamber, the right ventricle (RV). Leads 156 and 158 respectively connect IMD 150 with the RA and the RV. A remote indifferent can electrode may be formed as part of the outer surface of the IMD housing 152.

RA lead 156 is passed through a vein into the RA chamber. RA lead 156 is formed with a connector fitting into a connector bore of the IMD connector block 154 for electrically coupling a RA tip electrode 160 and RA ring electrode 162 to IMD internal circuitry via insulated conductors extending within the body of lead 156 for sensing a RA intracardiac electrogram (EGM) signal. Electrodes 160 and 162 may also be used for delivering cardiac pacing pulses in the RA during a pacing therapy that includes atrial pacing.

RA lead 156 may additionally carry PNS electrodes 164 and 166. In one embodiment electrodes 164 are used for stimulating the right phrenic nerve transveously in the area of the SVC. More proximal electrodes 166 are used for stimulating the left phrenic nerve transvenously in the area of the left innominate vein. In other embodiments, electrodes for stimulating phrenic nerves are carried by one or more additional leads coupled to IMD 150.

RV lead 158 is passed through the RA into the RV. The RV lead distal end carries RV tip electrode 170 and RV ring electrode 172 used for acquiring a RV EGM signal. Electrodes 170 and 172 may also be used in delivering RV pacing pulses, e.g. during bradycardia pacing, cardiac resynchronization therapy, or anti-tachycardia pacing therapy.

RV lead 168 may include a sensor 178 used for sensing venous pH or another correlate to venous blood carbon dioxide saturation. Venous blood pH may be used to regulate when measurements are taken for detecting ischemia and/or used in evaluating and interpreting measurements of a spontaneous breathing response associated with changes in induced respiration.

In FIG. 4, RV lead 168 also carries an RV coil electrode 174 and an SVC coil electrode 176 for use in delivering high voltage cardioversion/defibrillation shocks. RV lead 158 is formed with a proximal connector fitting into a corresponding connector bore of the IMD connector block 154 for electrically coupling electrodes 170, 172, 174 and 176 to IMD internal circuitry.

The electrodes 160, 162, 170, 172, 174, and 176 and the remote can electrode formed along housing 152 can be selectively employed to provide a number of unipolar and bipolar electrode combinations for acquiring atrial and ventricular signals and for delivering electrical pulses to the heart 180. IMD 150 is shown as a dual-chamber device capable of sensing and stimulation in an upper RA chamber and a lower RV chamber. It is understood that IMD 150 may be modified to operate as a single chamber device or bi-ventricular device for delivering ventricular therapies to one or both ventricular chambers with multi-chamber sensing in three or even all four heart chambers.

In some embodiments, a coronary sinus lead may extend from the IMD 150 into the coronary sinus and further into a cardiac vein to position one or more electrodes for sensing and pacing in the left ventricle. A coronary sinus lead may include one or more electrodes positioned adjacent to the left atrium for pacing and sensing in the left atrium. Furthermore, it is recognized that embodiments may be practiced in a single chamber, dual chamber or multi-chamber implantable cardiac device that does not include cardioversion and defibrillation functions.

Leads 156 and 158 and IMD housing 152 may further include other sensors besides pH sensor 178 and the electrodes shown, which may sense electrical signals, including impedance signals. Other sensors may include A pressure sensor, accelerometer, optical sensor, acoustical sensor and blood gas sensor. These sensors may be variously used in monitoring induced respiration, monitoring spontaneous respiration, monitoring cardiac activity, and monitoring patient activity and/or posture. Sensor signals may be used in regulating when ischemia monitoring is performed and/or in normalizing or interpreting a spontaneous breathing response to induced respiration for detecting ischemia.

Figure 5:
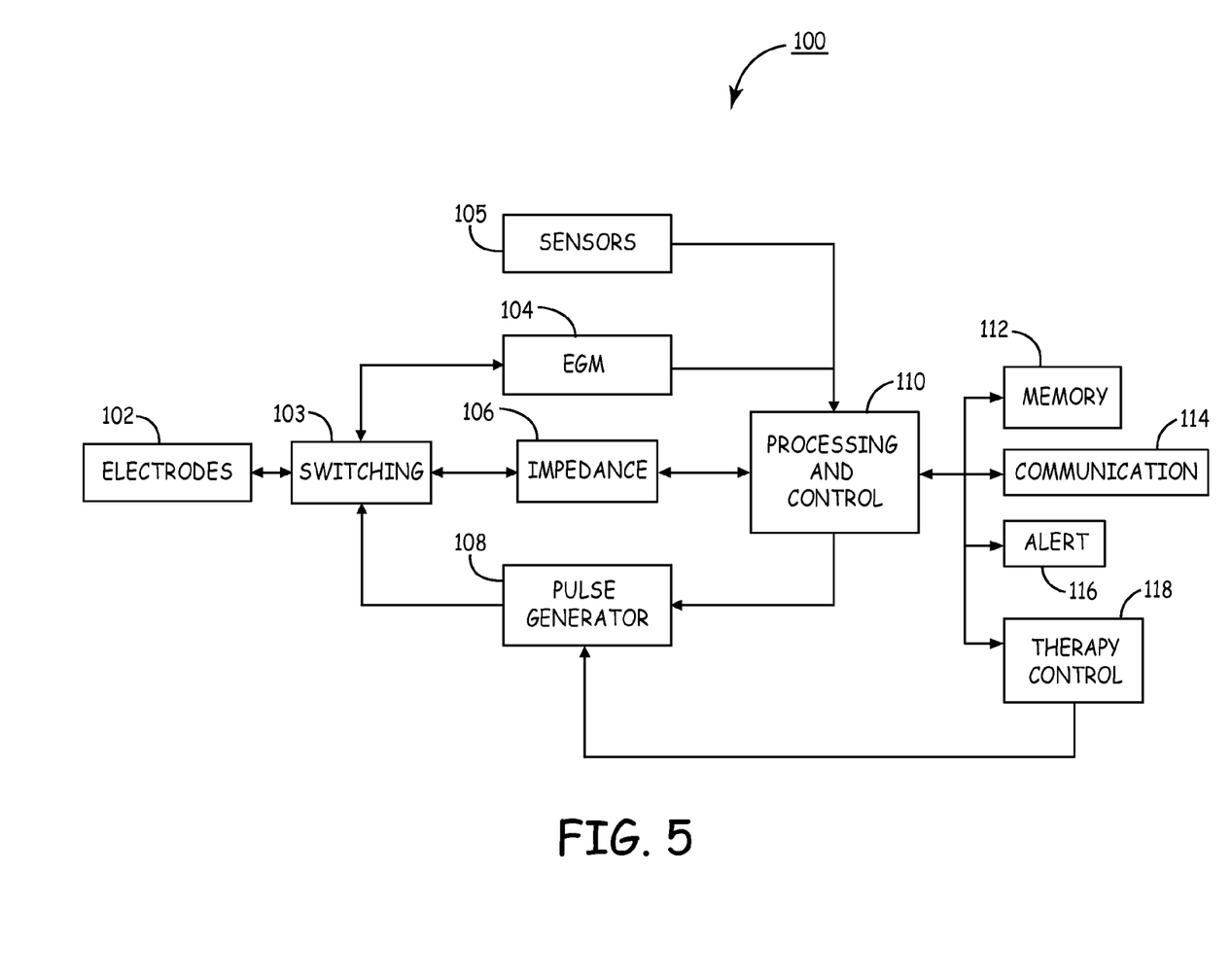
FIG. 5 is a functional block diagram of an IMD configured to detect ischemia.

FIG. 5 is a functional block diagram of an IMD 100 configured to detect ischemia. IMD 100 may correspond generally to any of the IMD systems shown in FIGS. 1 through 4. Electrodes 102 are coupled to EGM sensing 104, impedance sensing 106, and pulse generator 108 via switching circuitry 103. Electrodes 102 may correspond to any of the electrodes shown in FIGS. 1 through 4 or other electrodes carried along one or more leads for delivering PNS, sensing cardiac signals, and optionally delivering a cardiac stimulation therapy. Electrodes 102 may further include other electrodes available along the IMD housing and any other subcutaneous or cardiac leads coupled to IMD 100.

Electrodes 102 are selected via switching circuitry 103 for coupling to EGM sensing circuitry 104 to sense cardiac activity. Electrodes 102 may also be selected in pairs as an impedance signal drive current pair and impedance measurement electrode pair(s) via switching circuitry 103 for monitoring thoracic impedance by impedance monitoring circuitry 106. Electrodes 102 are further selected via switching circuitry 103 for delivering PNS pulses generated by pulse generator 108. In some embodiments, pulse generator 108 may provide therapeutic pulses, such as cardiac pacing pulses in addition to the PNS pulses used in the detection of ischemia. In addition to using PNS to detect ischemia, PNS pulses may be delivered according a respiration therapy protocol in response to an ischemia detection.

EGM sensing circuitry 104 is provided for sensing cardiac events, detecting arrhythmias, and may be used in controlling the timing of PNS pulses during cardiac refractory. Cardiac events detected from EGM signals may also be used in controlling when ischemia monitoring is performed.

The impedance sensing circuitry 106 includes drive current circuitry and impedance measurement circuitry for monitoring thoracic impedance. The thoracic impedance measurements can be used to select optimal electrodes and stimulation parameters for achieving a desired effect on respiration caused by PNS. Impedance sensing circuitry 106 may be used to monitor a spontaneous breathing response to the induced respiration for use in detecting ischemia. Examples of thoracic impedance measurement methods that can be used for monitoring a respiration signal are generally described in U.S. Pat. No. 4,901,725 (Nappholz), U.S. Pat. No. 6,076,015 (Hartley), and U.S. Pat. No. 5,824,029 (Weijand, et al), all of which are hereby incorporated herein by reference in their entirety. As will be further described below, minute ventilation, which may be estimated using an thoracic impedance signal may be measured using impedance sensing circuitry 106 and used in interpreting a spontaneous breathing response to PNS.

Other physiological sensors 105 may be included for sensing physiological signals correlated to respiration for monitoring induced respiration and spontaneous respiration for detecting ischemia. Other sensors 105 may include a pressure sensor, EMG electrodes for monitoring diaphragm activation, accelerometer, or air flow sensor, among others, for sensing a respiratory response to PNS and spontaneous breathing response before, during or after induced respiration. Other sensor signals may be substituted or used in addition to thoracic impedance signal monitoring for use in monitoring respiration during ischemia detection methods.

Additional sensors used in monitoring a spontaneous breathing response to an induced respiration intervention for detecting ischemia may include measuring venous or arterial pH, venous $CO_2$, and patient activity. Devices and methods for measuring pH or correlates to $CO_2$ in blood are generally disclosed in U.S. Pat. No. 4,694,834 (Meyerhoff, et al.) and U.S. Pat. No. 5,047,208 (Schweitzer, et al.), both of which patents are hereby incorporated herein by reference in their entirety. The use of an activity sensor in an implantable medical device is generally disclosed in U.S. Pat. No. 5,231,986 (Bennett), hereby incorporated herein by reference in its entirety.

Processing and control 110 receives signals from EGM sensing 104, sensors 105, and impedance sensing circuitry 106. Processing and control 110 controls pulse generator 108 to deliver PNS pulses using selected electrodes 102 to induce respiration. Sensors 105 and or impedance sensing 106 provide a signal correlated to respiration to processing and control 110 for detecting ischemia.

Device 100 may include a therapy delivery module, including, for example, therapy control circuitry 118 and pulse generator 108. A therapy delivery module may include a drug delivery or biological fluid delivery pump and associated catheter in other embodiments. In response to received signals, processing and control 110 controls therapy control 118. Therapy control 118 controls pulse generator 108 to deliver a therapy, which may include a respiration therapy in which PNS pulses are delivered, and/or a cardiac therapy in which pacing pulses or cardioversion/defibrillation shocks are delivered by pulse generator 108 using electrodes 102 selected by switching circuitry 103. Therapy control 118 may control the timing, rate, pulse amplitude, and other parameters used to control the therapy delivery.

Processing and control 110 may be embodied as a programmable microprocessor and associated memory 112. Received signals used by processing and control 110 in controlling IMD function may additionally include user command signals received by communication circuitry 114 from an external programming device and used to program processing and control 110. Processing and control 110 may be implemented as any combination of an application specific integrated circuit (ASIC), an electronic circuit, a processor (shared, dedicated, or group) and memory that execute one or more software or firmware programs, a combinational logic circuit, or other suitable components that provide the described functionality.

Memory 112 stores data associated with the monitored signals. Data may be transmitted to an external device by communication circuit 114, which typically includes wireless transmitting and receiving circuitry and an associated antenna for bidirectional communication with an external device. Processing and control 110 may generate reports or alerts relating to ischemia monitoring and detection that are transmitted by communication circuitry 114.

Alert circuitry 116 may be provided for generating a patient alert signal to notify the patient or a clinician of a condition warranting medical attention, particularly an ischemic condition detected by processing and control 110. In one embodiment, an alert is generated in response to sensing ischemia based on a spontaneous breathing response associated with PNS. The patient may be alerted via an audible sound, perceptible vibration, IMD pocket stimulation, or the like and be advised to seek medical attention upon perceiving an alert signal. A clinician alert may be transmitted by communication circuit 114 to an external device, such as a programmer or home monitor and optionally along a communication network to a desired designation.

In some embodiments, a therapeutic response to ischemia detection may be provided under the control of therapy control 118. A therapeutic response may include a respiration therapy in which PNS is delivered to increase a respiration rate and/or tidal volume. A therapeutic response may alternatively or additionally include a cardiac stimulation therapy, such as cardiac pacing or cardiac resynchronization therapy or an anti-arrhythmia therapy.

Figure 6:
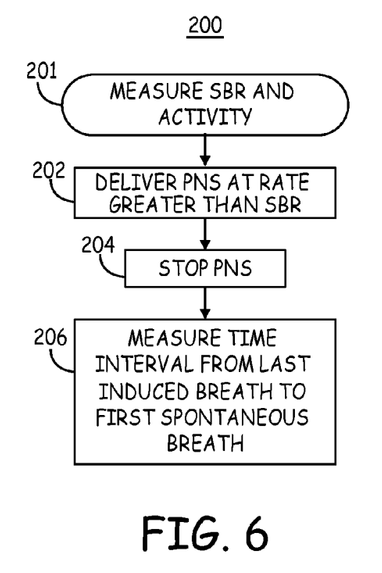
FIG. 6 is a flow chart of a method for measuring a spontaneous breathing response to induced respiration for use in detecting ischemia according to one embodiment.

FIG. 6 is a flow chart 200 of a method for measuring a spontaneous breathing response to induced respiration for use in detecting ischemia according to one embodiment. Ischemia, in particular ischemia affecting the CNS and more specifically ischemia of the subcerebral structures of the CNS involved in controlling respiration, is detected by measuring a spontaneous breathing response to stimulation delivered to induce activation of the diaphragm.

Flow chart 200 and other flow charts presented herein are intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 201, the spontaneous breathing rate and patient activity are measured and recorded. The spontaneous breathing rate (SBR) may be recorded using a thoracic impedance signal or other signal that varies cyclically in correlation with a patient's respiration. The patient's activity level may be measured using an accelerometer, which may be incorporated in the housing of the IMD.

At block 202, the diaphragm is activated to induce respiration using PNS. PNS is delivered using suprathreshold pulse trains delivered at a rate that is greater than the SBR. PNS is delivered to induce respiration for a predetermined interval of time, for example an interval of approximately 10 seconds to 60 seconds. In some embodiments the interval of stimulation may be approximately 10 to approximately 30 seconds, and more typically approximately 15 to 20 seconds.

The PNS is stopped at block 204 upon expiration of the predetermined time interval. Upon stopping PNS, a time interval is measured until the first spontaneous breath. This time interval is a measurement of the spontaneous breathing response to modulation of the blood oxygen and carbon dioxide levels by an induced respiration intervention. Changes in this measurement of the spontaneous breathing response over time, particularly under similar baseline SBR, activity, venous pH and venous $CO_2$, conditions, can be used as an indication of subcerebral ischemia. In particular, a shorter interval of time measured at block 206, under similar conditions activity or other indicators of patient metabolic demand, would indicate an earlier impulse to breathe, i.e. greater sensitivity to blood carbon dioxide levels, which is indicative of ischemia. The time interval measurement may be expressed as a ratio of the measured time interval to a respiration period caused by PNS.

In some embodiments, the time interval measured at block 206 may be stored with or normalized by the spontaneous breathing rate and/or activity measured at block 201. Alternatively, the initial spontaneous breathing rate and patient activity measurements at block 201 may be used to verify that repeated measurements of the time interval (at block 206) taken over time for detecting ischemia are taken during similar initial spontaneous breathing rate and/or patient activity conditions.

In addition to or alternatively to the time interval measured between the last induced breath and the first spontaneous breath, the rate at which spontaneous breathing returns after stopping PNS may be measured and stored at block 206. This rate may be compared to the rate measured at block 201 and a rate ratio or difference may be used as a spontaneous breathing response measurement for detecting ischemia.

Figure 7:
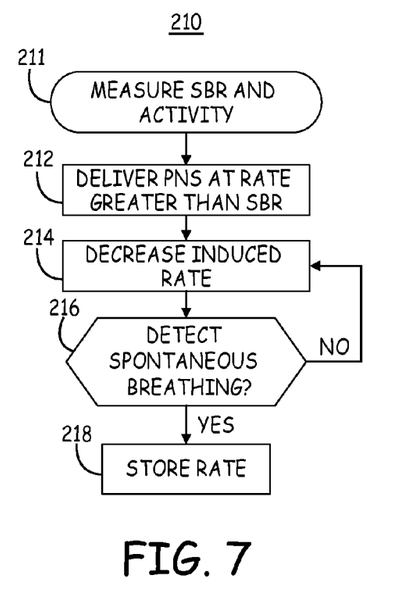
FIG. 7 is a flow chart of a method for measuring a spontaneous breathing response to induced respiration for monitoring for ischemia according to an alternative embodiment.

FIG. 7 is a flow chart 210 of a method for measuring a spontaneous breathing response to induced respiration for monitoring for ischemia according to an alternative embodiment. At block 211, the SBR and patient activity are measured. As described above, SBR and/or patient activity may be used to regulate when a spontaneous breathing response is measured for use in detecting ischemia, normalizing a spontaneous breathing response measurement, and/or recording with a spontaneous breathing response measurement for use by a clinician interpreting trends in spontaneous breathing response measurement data over time.

At block 212, PNS is delivered at a rate greater than the measured SBR. PNS is delivered to induce respiration at a rate at which spontaneous respiration disappears. PNS is delivered using trains of pulses having a supra-threshold pulse amplitude to ensure depolarization of the phrenic nerves. The induced respiration rate is gradually reduced by slowing the PNS pulse train rate at block 214. PNS may be delivered at a given rate for a predetermined time interval, e.g. 30 seconds or more. If spontaneous breathing does not return, the PNS is reduced again until spontaneous breathing returns, as determined at block 216. The PNS rate at which spontaneous breathing returns is recorded at block 218 as a measurement of the spontaneous breathing response to PNS for use in detecting ischemia. The rate of spontaneous breathing, when it is detected to return, may additionally or alternatively be recorded at block 218.

Figure 8:
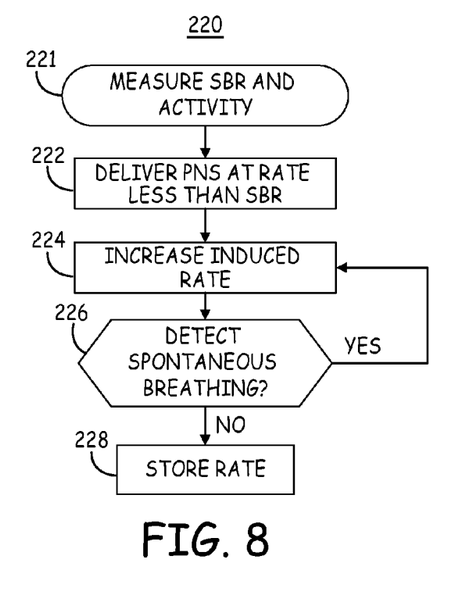
FIG. 8 is a flow chart of a method for measuring a spontaneous breathing response to induced respiration according to yet another embodiment.

FIG. 8 is a flow chart 220 of a method for measuring a spontaneous breathing response to induced respiration according to yet another embodiment. At block 221, the initial SBR and patient activity are measured as described previously. At block 222, PNS is delivered at a rate below the SBR. The PNS rate is increased at block 224 in a step-wise manner until spontaneous breathing disappears, as determined at block 226. The PNS rate at which spontaneous breathing is no longer present is recorded as a spontaneous breathing response measurement at block 228. As indicated previously, the rate may be normalized by the initial SBR, patient activity or stored with this data to allow better interpretation of the spontaneous breathing response.

FIGS. 6 through 8 illustrate various methods of measuring a spontaneous breathing response to induced respiration. A spontaneous breathing response may be measured during or after the induced respiration intervention as a rate or other parameter of the PNS at which a change in spontaneous breathing occurs. In other embodiments, measurement of a spontaneous breathing response to induced respiration may include measuring a tidal volume or correlate thereof of spontaneous breaths and/or induced breaths when spontaneous breathing first reappears.

In FIGS. 6 through 8, the spontaneous breathing response measurement is taken when an induced respiration rate is changed (increased, decreased, or stopped). In other embodiments, the induced respiration intervention may include changing stimulation amplitude, number of pulses in a pulse train, frequency of pulses in a pulse train, or other stimulation control parameters that affect the induced respiration tidal volume. The spontaneous breathing response measurement may be measured when the induced respiration tidal volume is changed instead of, or in addition to, a change in the induced respiration rate.

In FIG. 6 through 8 the SBR and activity are measured initially to provide measurements under controlled conditions and/or normalization parameters to allow a spontaneous breathing response to be compared over time. In alternative embodiments, other indicators of patient metabolic demand may be measured such as blood pH or minute ventilation. The spontaneous breathing response measurements may be obtained over time, along with measurements of baseline SBR, heart rate, patient activity, blood pH, blood gases, or other measurements associated with the metabolic demand of the patient. Trends in the spontaneous breathing response as a function of any of these parameters may be monitored to detect a change in the spontaneous breathing response. A change in the spontaneous breathing response is used to detect an ischemic condition.

Figure 9:
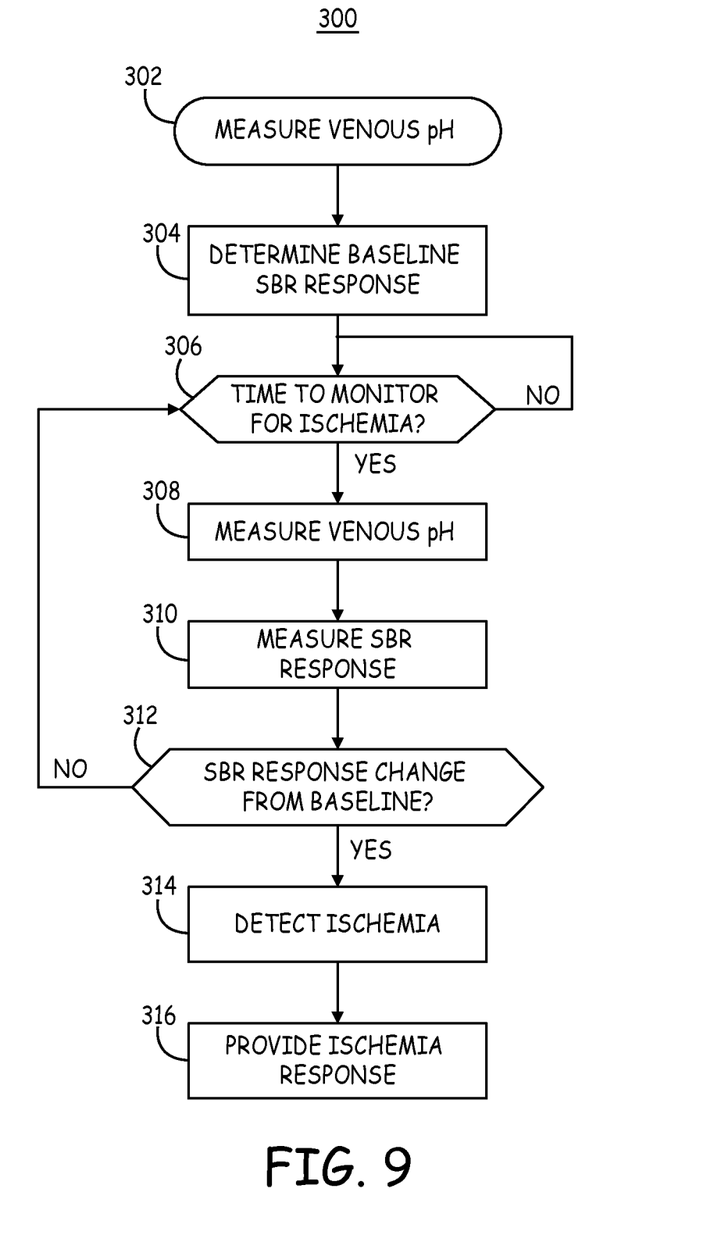
FIG. 9 is a flow chart of a method for detecting ischemia according to one embodiment.

FIG. 9 is a flow chart 300 of a method for detecting ischemia according to one embodiment. At block 302, venous pH is measured to determine a baseline measurement. At block 304, a baseline SBR response to a change in induced respiration is measured. The SBR response may be measured according to any of the methods described in conjunction with FIGS. 6 through 8. The SBR response may be measured as a time interval from a last induced breath to a first spontaneous breath, an induced respiration rate at which spontaneous breathing disappears as the induced rate is being increased, or an induced respiration rate at which spontaneous breathing appears as the induced rate is being decreased, or any combination thereof. The baseline SBR response is stored for future comparison.

At block 306, the control processor determines if an ischemia monitoring time is reached, the venous pH is measured again at block 308. In some embodiments, a time for ischemia monitoring is determined according to a predetermined schedule or in response to a user command. In other embodiments, the IMD control processor may determine that it is time to monitor for ischemia in response to another physiological signal or detected event. For example, ischemia monitoring may be performed in response to detecting an arrhythmia, low arterial oxygen saturation, thoracic edema, low blood pressure or other parameter indicative of a worsening hemodynamic status, increased venous pH, apnea or other disordered breathing pattern, or any other physiological condition that may be associated with a possible ischemic episode.

The venous pH measurement may be repeated at block 308 for regulating when the SBR response is measured so that the SBR response is measured under similar conditions as the baseline response measurement. Alternatively, the venous pH measurement may be used in normalizing a SBR response measurement for comparison to the baseline SBR response measurement or for detecting a SBR response trend as a function of pH. The recorded pH provides additional information to a clinician in evaluating the SBR response measurements.

At block 310, the SBR response is measured using the same measurement technique used to obtain the baseline measurement at block 304. As described above, performing the SBR response measurement includes modulating blood oxygen and carbon dioxide by inducing respiration via PNS and determining a spontaneous breathing response to the induced respiration intervention.

At block 312, the measured response is compared to the baseline response for automatic detection of ischemia. If the SBR response has changed from the baseline, ischemia is detected at block 314. In particular, if the SBR response indicates a higher sensitivity to venous pH, ischemia is detected. A higher sensitivity may be indicated by a shorter interval to the onset of spontaneous breathing upon terminating induced respiration, a higher induced rate at which spontaneous breathing is still present or returns as the induced rate is adjusted, or a higher spontaneous breathing rate or tidal volume associated with a response to adjustments in induced respiration.

If ischemia is detected automatically, an ischemia response may be provided at block 316. An ischemia response may include generating a patient alert and/or transmitting clinician notification. An ischemia response may include adjusting a therapy, such as a cardiac pacing or anti-arrhythmia therapy, a drug therapy, a respiration therapy or other therapy automatically delivered by a medical device system that can potentially improve or alleviate the ischemic episode.

If a change from the baseline SBR response indicative of ischemia is not detected at decision block 312, the process returns to block 306 to wait for the next ischemia monitoring session. The baseline SBR response may be repeated periodically, and a trend in the SBR response over time may be monitored.

Figure 10:
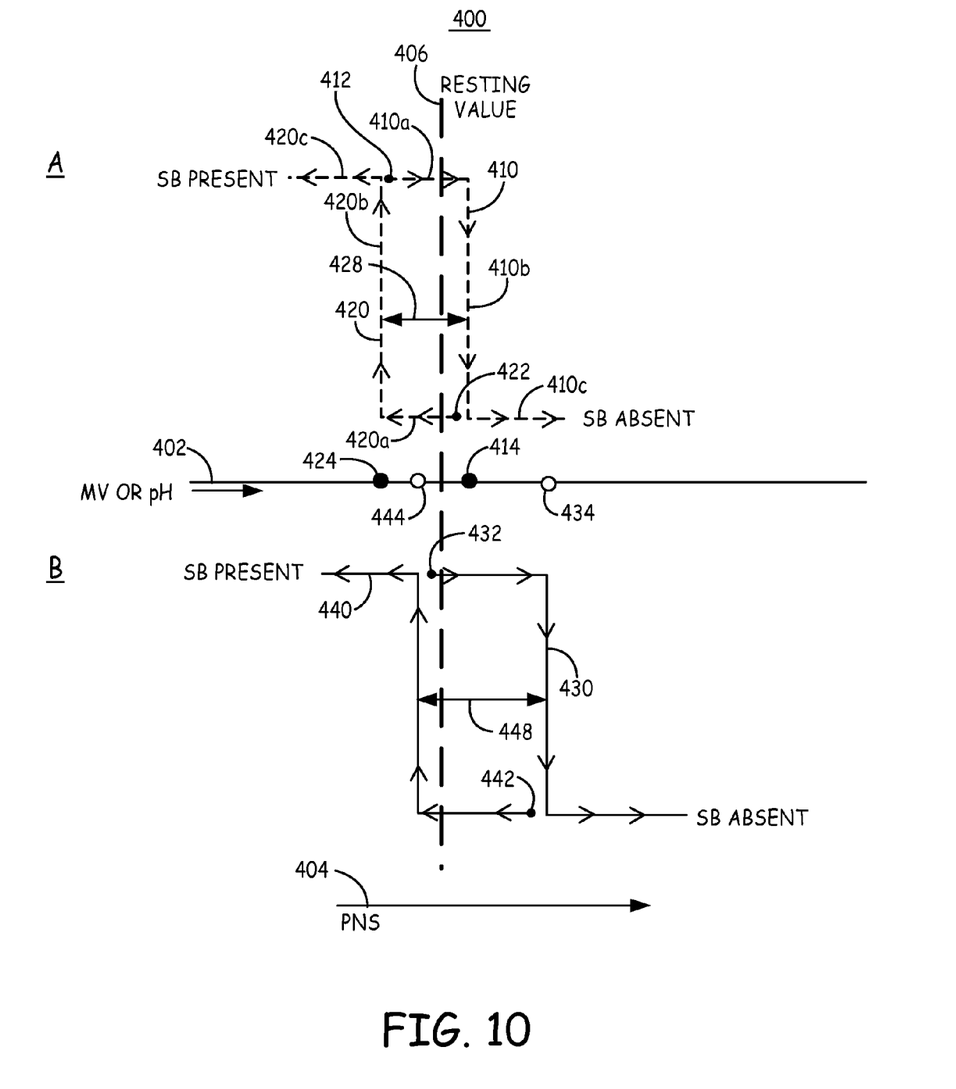
FIG. 10 shows illustrative plots of spontaneous breathing responses to changing phrenic nerve stimulation in the presence and absence of subcerebral ischemia.

FIG. 10 shows illustrative plots 400 of spontaneous breathing responses to changing PNS in the presence and absence of subcerebral ischemia. An indicator of the metabolic status of the patient measured prior to or at the onset of PNS is plotted along the horizontal axis 402. The metabolic status may be measured as minute ventilation (MV) or venous (or arterial) pH or another correlate to the metabolic status of the patient. The vertical line 406 indicates a normal resting value of the metabolic status parameter for the given patient.

The top panel A corresponds to a spontaneous breathing response in the absence of ischemia. The bottom panel B corresponds to a spontaneous breathing response in the presence of ischemia.

Arrow 404 indicates the direction of increasing PNS applied during an ischemia monitoring episode from which the plots shown in panel A and B are generated. PNS is typically increased by increasing the induced respiration rate. PNS may additionally or alternatively be increased by increasing an induced tidal volume through increases in stimulation pulse amplitude, pulse number and/or pulse train frequency.

A metabolic status parameter plotted along the horizontal axis 402 represents the metabolic status parameter measured just prior to or at the onset of PNS. The metabolic status indicator is determined to examine the sensitivity of the subcerebral structures to pH and carbon dioxide levels as an indication of ischemia. The metabolic status parameter plotted along axis 402 is being measured when changes in spontaneous breathing occur in response to changes in PNS as further described hereafter.

In a first plot 410, a spontaneous breathing response is measured in the absence of ischemia. PNS is initiated at a relatively low level, which may correspond to a breath rate and/or tidal volume at or below the intrinsic breath rate and tidal volume. For example, PNS may be initiated at a low rate 412 below an intrinsic spontaneous breathing rate.

PNS is gradually increased to increase a rate of induced respiration as indicted by the right-pointing arrows along the top horizontal portion 410a of plot 410. When PNS is initiated, spontaneous breathing (SB) is present and remains present as PNS is initially increased. SB disappears, as indicated by the down-pointing arrows along vertical portion 410b of plot 410, when the PNS rate reaches a level that is beyond the metabolic needs of the patient. The metabolic status parameter measurement 414 at the time SB disappears is measured. SB remains absent with further increases in PNS as indicated by the horizontal portion 410c of plot 410.

The SB response plot 420 in Panel A is obtained when the PNS is decreased from an initially high level 422 at which no SB is present. PNS is decreased (along horizontal portion 420a) until SB returns, as indicated by the vertical portion 420b with upward-pointing arrows. The metabolic status parameter measurement 424 is recorded when SB reappears. SB remains present as PNS continues to be reduced (horizontal portion 420c).

As such, when PNS is increased from an initially low level, SB disappears at some PNS level that corresponds to a metabolic status parameter value 414 that is greater than the normal resting value 406. There is a hysteresis in the SB response such when PNS is started at a high level and decreased SB reappears at a value 424 that is lower than the value 414 of the metabolic status parameter at which SB disappeared. The measurements 424 and/or 414, or a difference 428 between these values obtained when ischemia is known not to be present, can be used as a baseline measurement for comparative analysis in future ischemia detection. These measurements 414 and/or 424 may be used in conjunction with the PNS parameters at which SB reappears and/or disappears for detecting ischemia.

In the lower panel B, ischemia is present. The plot 430 corresponding to increasing PNS until SB disappears and the plot 440 corresponding to decreasing PNS until SB reappears are both shifted to the right relative to plots 410 and 420 in panel A obtained in the absence of ischemia.

Plot 430 is obtained when PNS is started at an initial rate 432 at or near the SBR and therefore does not immediately cause SB to disappear. PNS is increased until SB disappears and the metabolic measurement 434 is recorded. Plot 440 is obtained when PNS is started at an initially high level 442. PNS is decreased until SB reappears and the metabolic status parameter measurement 444 is recorded.

The metabolic parameter status values 434 and 444 are relatively higher when ischemia is present than respective analogous values 414 and 424 when ischemia is absent. Additionally, the difference 448 between measurements 434 and 444 is greater than the difference 428 between measurements 414 and 424. These changes in the SB response occur due to an increased sensitivity of the subcerebral structures to blood pH and carbon dioxide levels associated with ischemia.

As such, a shift in one or both of the measurements 434, 444 relative to respective baseline measurements 414, 424 or the resting value 406 can be used to detect subcerebral ischemia. Additionally or alternatively an increase in difference 448 relative to difference 428 can be used to detect subcerebral ischemia. A logical combination of criteria relating to any of the measurements 434 and 444, the PNS level at which SB disappears, the PNS level at which SB reappears, a time interval after stopping PNS that SB reappears or other spontaneous breathing response measurements may be used in detecting subcerebral ischemia.

Figure 11:
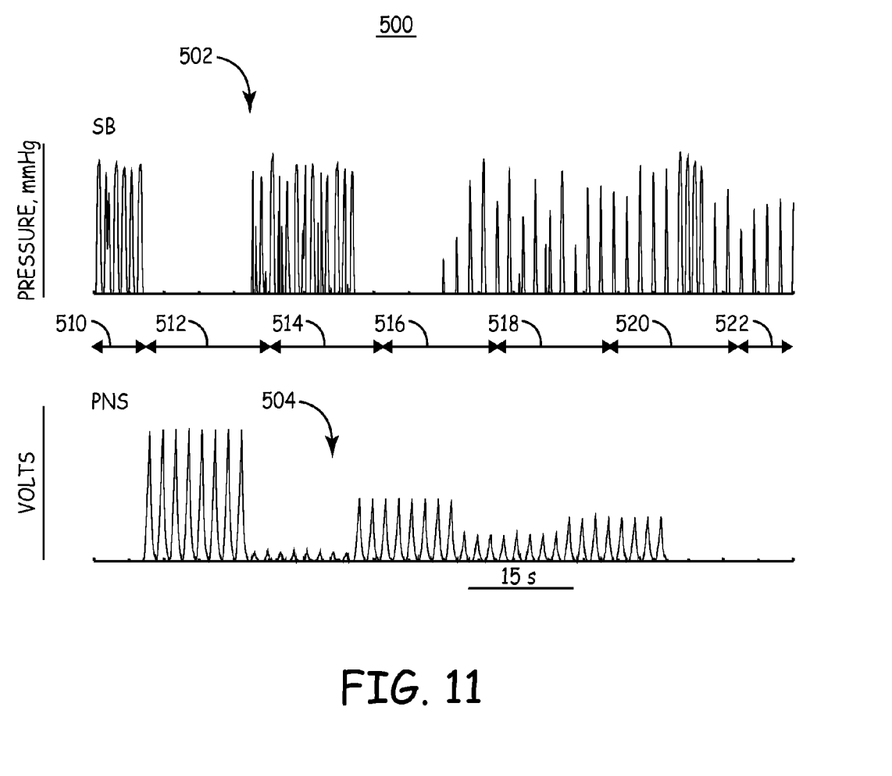
FIG. 11 is a time-based plot of a spontaneous breathing response to varying phrenic nerve stimulation.

FIG. 11 is a time-based plot 500 of a spontaneous breathing response 502 to varying PNS 504. SB 502 is measured as the expired $CO_2$ pressure in mmHg using a capnograph. The amplitude of PNS 504 is plotted over time. The SB response 502 is elicited by changes in PNS pulse amplitude. Other PNS parameters remained constant, such as rate and pulse number. During an initial time interval 510, no PNS is delivered. SB is present at a baseline rate. PNS is delivered at a suprathreshold amplitude during time interval 512. During this high level of PNS, SB disappears.

During time interval 514, PNS is delivered using a subthreshold pulse amplitude. SB returns near its initial rate and tidal volume. During the next time intervals 516, 518, and 520 PNS is delivered at varying stimulation amplitudes (relative to a stimulation threshold) with a varying SB response. During time interval 516, the highest pulse amplitude PNS is delivered out of the three intervals 516, 518, and 520 and SB is substantially absent. During the time intervals 518 and 520, the relatively lower pulse amplitudes result in some degree of capture and induced respiration but not enough to cause SB to disappear entirely. During the last time interval 522, PNS is withheld, and SB reappears near the initial baseline rate and tidal volume.

Pulse amplitude represents one PNS parameter that can be varied to vary the level of PNS being delivered and the resulting induced respiration. PNS pulse amplitude can be increased until SB disappears and again decreased until SB reappears. At the point that SB disappears and reappears, blood pH, SB minute ventilation, or another metabolic status parameter may be measured to obtain data similar to that shown in FIG. 10 for detecting ischemia.

Figure 12:
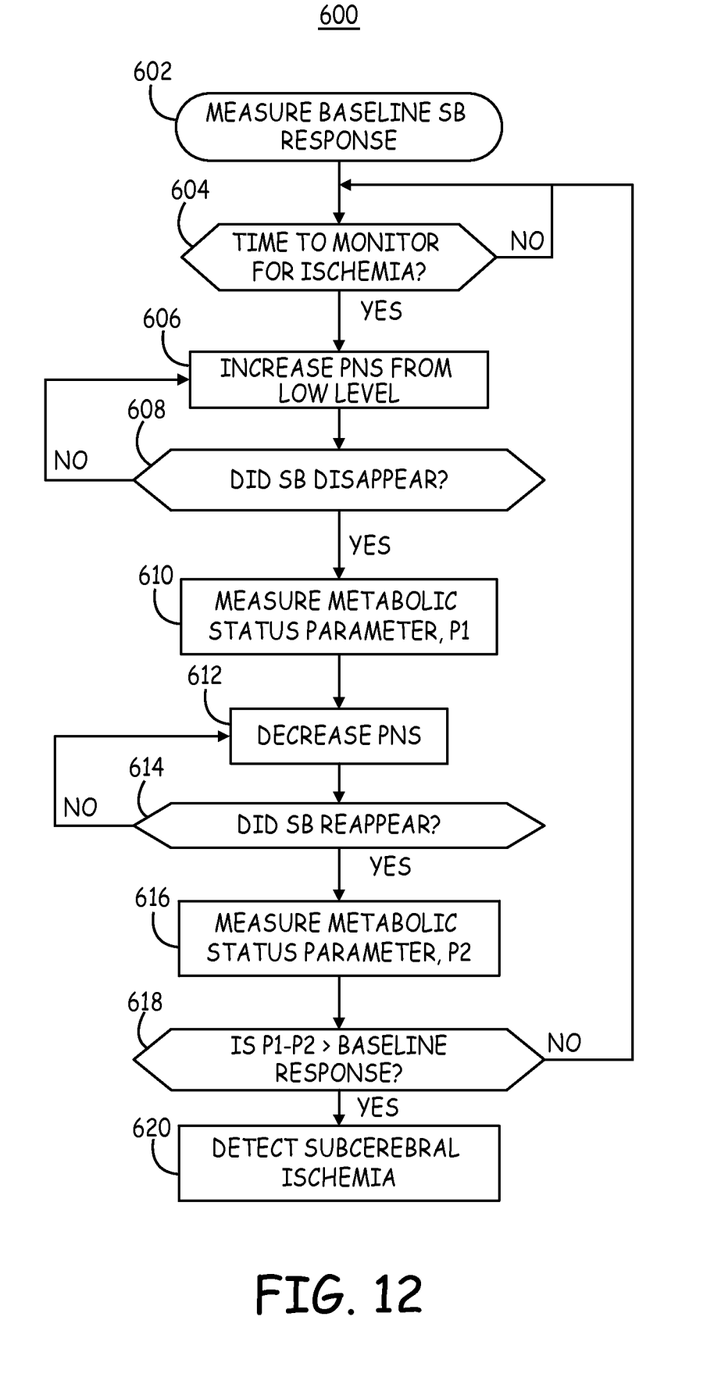
FIG. 12 is a flow chart of a method for detecting subcerebral ischemia using according to one embodiment.

FIG. 12 is a flow chart of a method for detecting subcerebral ischemia using PNS according to one embodiment. At block 602 a baseline SB response is measured. The baseline response may be established as generally described in conjunction with FIG. 10, above, with reference to top panel A. Establishing the baseline response includes measuring at least one of a PNS level at which SB disappears, a PNS level at which SB reappears, a time interval from stopping PNS till SB appears, a metabolic status parameter at the time point that SB disappears or reappears, or any combination thereof.

As such, measuring the baseline SB response may include delivering PNS in an increasing manner, in a decreasing manner, or both (or starting and stopping PNS). In one embodiment, PNS is started at a low level, increased until SB disappears then decreased until SB reappears. The metabolic status parameter is measured at both the time point SB disappears and the time point SB reappears. Depending on the metabolic status parameter being measured, it is recognized that the measurement at "a time point" may be relatively instantaneous or may require one or more respiration cycles.

At block 604, a determination is made whether it is time to monitor for ischemia, which may be based on scheduled intervals, a scheduled time of day, a triggered response to other sensed physiological signals, or starting, stopping or adjusting a therapy. It is recognized that a baseline SB response may be updated by returning to block 602, for example on a periodic basis, when ischemia monitoring has not been started.

If it is time to start ischemia monitoring, the SB response is measured in the same manner as the method used to obtain the baseline SB response at block 602. In one embodiment, PNS is increased from a low level at block 606. The low level may be a level that results in an induced rate or tidal volume less than spontaneous breathing. If SB does not disappear, as determined at decision block 608, PNS is again increased at block 606 until SB does disappear. The presence or absence of SB may be sensed using numerous methods such as, but not limited to, measuring a thoracic impedance signal, a thoracic pressure signal, a diaphragm EMG, an acoustical signal, or an accelerometer signal.

When SB disappears, a metabolic status parameter, such as MV or blood pH, is measured to obtain point P1 (which is analogous to point 434 in FIG. 10) at block 610. After obtaining P1, PNS is decreased at block 612 until SB reappears as determined at block 614. The metabolic status parameter measurement is repeated at block 616 to obtain point P2 (analogous to point 444 in FIG. 10).

At decision block 618, a difference between P1 and P2 is compared to the analogous difference obtained as the baseline SB response at block 602. If the difference between P1 and P2 has increased compared to baseline, subcerebral ischemia is detected at block 620. It is recognized that the criterion applied at block 618 may include comparing P1-P2 to a percentage of the baseline or some threshold range above the baseline to detect a clinically relevant change in P1-P2. In other embodiments, any of the comparisons described above in conjunction with FIG. 10 for detecting ischemia may be used in place of or in addition to the difference comparison shown at block 618.

If ischemia is detected at block 620, a response to ischemia may be provided as previously described in conjunction with FIG. 9. If the criterion (or criteria) for detecting ischemia are not met at block 618, the process returns to block 604 to wait for the next ischemia monitoring time. In some embodiments, the stored baseline SB response measurements may be updated using the measurements of P1 and P2 obtained at blocs 610 and 616, respectively, when ischemia is not detected based on criteria applied at block 618.

Thus, a method and apparatus for detecting ischemia have been presented in the foregoing description with reference to specific embodiments. It is appreciated that various modifications to the referenced embodiments may be made without departing from the scope of the disclosure as set forth in the following claims.

The invention claimed is:

1. A method for detecting ischemia, the method comprising:
    delivering stimulation to a phrenic nerve to induce respiration;
    determining a spontaneous breathing response to stimulation;
    detecting ischemia in response to the spontaneous breathing response;
    adjusting a parameter controlling delivery of the stimulation;
    detecting a change in spontaneous breathing in response to adjusting the parameter; and
    comparing the change in spontaneous breathing to a previously detected change in spontaneous breathing determined in response to adjusting the parameter,
    the ischemia detected in response to the comparison.

2. A method for detecting ischemia, the method comprising:
    delivering stimulation to a phrenic nerve to induce respiration;
    determining a spontaneous breathing response to stimulation; and
    detecting ischemia in response to the spontaneous breathing response,
wherein adjusting the parameter comprises at least one of increasing a stimulation rate, decreasing a stimulation rate, starting stimulation, stopping stimulation, adjusting a stimulation pulse amplitude, adjusting a stimulation pulse number, and adjusting a stimulation pulse train frequency.

3. A method for detecting ischemia, the method comprising:
    delivering stimulation to a phrenic nerve to induce respiration;
    determining a spontaneous breathing response to stimulation; and
    detecting ischemia in response to the spontaneous breathing response,
wherein determining the spontaneous breathing response comprises determining a spontaneous breathing response measurement by determining at least one of a stimulation parameter at which spontaneous breathing disappears, a stimulation parameter at which spontaneous breathing reappears, a time interval between a stimulation induced breath and a spontaneous breath, a spontaneous breathing rate, a spontaneous breathing tidal volume, and a parameter indicative of a metabolic status of the patient.

4. A method for detecting ischemia, the method comprising:
    delivering stimulation to a phrenic nerve to induce respiration;
    determining a spontaneous breathing response to stimulation; and
    detecting ischemia in response to the spontaneous breathing response,
    measuring a parameter correlated to venous pH,
    wherein detecting ischemia comprises identifying a change in a sensitivity of the spontaneous breathing response to venous pH compared to a previous spontaneous breathing response.

5. A method for detecting ischemia, the method comprising:
    delivering stimulation to a phrenic nerve to induce respiration;
    determining a spontaneous breathing response to stimulation; and
    detecting ischemia in response to the spontaneous breathing response,
wherein determining the spontaneous breathing response comprises:
    measuring a first value of a metabolic status parameter corresponding to a disappearance of spontaneous breathing in response to the stimulation inducing respiration;
    measuring a second value of the metabolic status parameter corresponding to a reappearance of spontaneous breathing in response to adjusting the stimulation inducing respiration; and
    detecting a shift of at least one of the first value and the second value relative to a value of the metabolic status parameter previously measured during a known non-ischemic condition;
    the ischemia being detected in response to the detected shift.

6. The method of claim 5, wherein the metabolic status parameter comprises at least one of a blood pH and a minute ventilation.

7. A medical device for detecting ischemia, comprising:
    a medical lead for delivering stimulation to induce respiration;
    a sensor sensing a signal correlated to patient respiration;
    a control processor configured to receive the sensor signal, determine a spontaneous breathing response to the stimulation, and detect ischemia in response to the spontaneous breathing response,
        wherein the control processor is configured to adjust a parameter controlling delivery of the stimulation,
        detect a change in spontaneous breathing in response to adjusting the parameter, and
        compare the change in spontaneous breathing to a previously detected change in spontaneous breathing,
        the ischemia detected in response to the comparison.

8. The device of claim 7, further comprising a sensor for providing a signal to the control processor correlated to a metabolic status of the patient,
    wherein determining the spontaneous breathing response comprises determining a spontaneous breathing response measurement by determining at least one of a stimulation parameter at which spontaneous breathing disappears, a stimulation parameter at which spontaneous breathing reappears, a time interval between a stimulation induced breath and a spontaneous breath, a spontaneous breathing rate, a spontaneous breathing tidal volume, and a parameter indicative of a metabolic status of the patient.

9. A medical device for detecting ischemia, comprising:
    a medical lead for delivering stimulation to induce respiration;
    a sensor sensing a signal correlated to patient respiration;

a control processor configured to receive the sensor signal, determine a spontaneous breathing response to the stimulation, and detect ischemia in response to the spontaneous breathing response, wherein the control processor is configured to adjust a parameter controlling delivery of the stimulation, detect a change in spontaneous breathing in response to adjusting the parameter, and compare the change in spontaneous breathing to a previously detected change in spontaneous breathing, the ischemia detected in response to the comparison, wherein adjusting the parameter comprises at least one of increasing a stimulation rate, decreasing a stimulation rate, starting stimulation, stopping stimulation, adjusting a stimulation pulse amplitude, adjusting a stimulation pulse number, and adjusting a stimulation pulse train frequency.

10. A medical device for detecting ischemia, comprising:
a medical lead for delivering stimulation to induce respiration;
a sensor sensing a signal correlated to patient respiration;
a control processor configured to receive the sensor signal, determine a spontaneous breathing response to the stimulation, and detect ischemia in response to the spontaneous breathing response; and
a pH sensor for measuring a parameter correlated to venous pH,
the control processor configured to receive the measured parameter,
wherein detecting ischemia comprises identifying a change in a sensitivity of the spontaneous breathing response to venous pH compared to a previous spontaneous breathing response.

11. A medical device for detecting ischemia, comprising:
a medical lead for delivering stimulation to induce respiration;
a sensor sensing a signal correlated to patient respiration;
a control processor configured to receive the sensor signal, determine a spontaneous breathing response to the stimulation, and detect ischemia in response to the spontaneous breathing response; and
a pH sensor for measuring a parameter correlated to venous pH,
the control processor configured to receive the measured parameter,
wherein detecting ischemia comprises identifying a change in a sensitivity of the spontaneous breathing response to venous pH compared to a previous spontaneous breathing response,
a sensor for providing a signal to the control processor correlated to a metabolic status parameter of the patient,
wherein determining the spontaneous breathing response comprises
measuring a first value of a metabolic status parameter corresponding to a disappearance of spontaneous breathing in response to the stimulation inducing respiration;
measuring a second value of the metabolic status parameter corresponding to a reappearance of spontaneous breathing in response to adjusting the stimulation inducing respiration; and
detecting a shift of at least one of the first value and the second value relative to a value of the metabolic status parameter previously measured during a known non-ischemic condition,
the ischemia being detected in response to the detected shift.

12. A medical device for detecting ischemia, comprising:
a medical lead for delivering stimulation to induce respiration;
a sensor sensing a signal correlated to patient respiration;
a control processor configured to receive the sensor signal, determine a spontaneous breathing response to the stimulation, and detect ischemia in response to the spontaneous breathing response; and
a pH sensor for measuring a parameter correlated to venous pH,
the control processor configured to receive the measured parameter,
wherein detecting ischemia comprises identifying a change in a sensitivity of the spontaneous breathing response to venous pH compared to a previous spontaneous breathing response,
a sensor for providing a signal to the control processor correlated to a metabolic status parameter of the patient,
wherein determining the spontaneous breathing response comprises
measuring a first value of a metabolic status parameter corresponding to a disappearance of spontaneous breathing in response to the stimulation inducing respiration;
measuring a second value of the metabolic status parameter corresponding to a reappearance of spontaneous breathing in response to adjusting the stimulation inducing respiration; and
detecting a shift of at least one of the first value and the second value relative to a value of the metabolic status parameter previously measured during a known non-ischemic condition,
the ischemia being detected in response to the detected shift,
wherein the metabolic status parameter comprises at least one of a blood pH and a minute ventilation.

13. The device of claim 12, further comprising circuitry for generating an alert signal in response to detecting ischemia.

14. The device of claim 12, further comprising a therapy delivery module,
the control processor further configured to adjust a therapy delivered by the therapy delivery module in response to detecting ischemia.

15. A computer-readable non-transitory medium storing instructions which cause a medical device to perform a method, the method comprising:
delivering stimulation to induce respiration;
determining a spontaneous breathing response to the stimulation;
detecting ischemia in response to the spontaneous breathing response;
adjusting a parameter controlling delivery of the stimulation;
detecting a change in spontaneous breathing in response to adjusting the parameter; and
comparing the change in spontaneous breathing to a previously detected change in spontaneous breathing determined in response to adjusting the parameter,
the ischemia detected in response to the comparison.

* * * * *